United States Patent [19]

D'Autry

[11] 4,141,250
[45] Feb. 27, 1979

[54] PLURAL PISTON, ADJUSTABLE DILUTING DEVICE HAVING A VOLUME INDICATOR ASSEMBLY

[76] Inventor: Eric M. D'Autry, 69-72 rue Gambetta, 95 Villiers-le-Bel, France

[21] Appl. No.: 792,810

[22] Filed: May 2, 1977

[30] Foreign Application Priority Data

May 10, 1976 [FR] France .................. 76 13939

[51] Int. Cl.² .................. G01N 1/14; G01F 11/06
[52] U.S. Cl. .................. 73/425.6; 222/43; 222/309
[58] Field of Search .................. 222/43, 46, 47, 134, 222/309; 73/425.4 P, 425.6; 128/218 C, 234; 23/253 R, 259

[56] References Cited

U.S. PATENT DOCUMENTS

| | | | |
|---|---|---|---|
| 3,013,435 | 12/1961 | Rodrigues, Jr. | 73/425.6 |
| 3,613,952 | 10/1971 | Gimont et al. | 222/309 X |
| 3,646,817 | 3/1972 | Hinchman et al. | 73/425.6 |
| 3,855,867 | 12/1974 | Roach | 73/425.6 |
| 4,054,062 | 10/1977 | Bronham | 73/425.6 |

FOREIGN PATENT DOCUMENTS

2287941 10/1974 France.

*Primary Examiner*—Stanley H. Tollberg
*Assistant Examiner*—Fred A. Silverberg
*Attorney, Agent, or Firm*—Mason, Kolehmainen, Rathburn & Wyss

[57] ABSTRACT

The invention provides an adjustable diluting device comprising a casing and a tapered tubular element or nose member, a volume-adjustment mechanism coupled with an indicator assembly, and a plunger unit movable in said casing; the plunger unit comprises a first piston having a central recess, a second piston adapted to slide in the recess with the interposition of a frictionally mounted joint, a sleeve for controlling the first piston, a shaft for controlling the second piston adapted to slide inside the sleeve, and a push button fixed to the upper end of the control shaft and adapted to cooperate with the upper end of the sleeve. The invention is particularly applied to the mixing of a determined volume of a liquid sample and of a determined volume of a liquid diluent.

10 Claims, 5 Drawing Figures

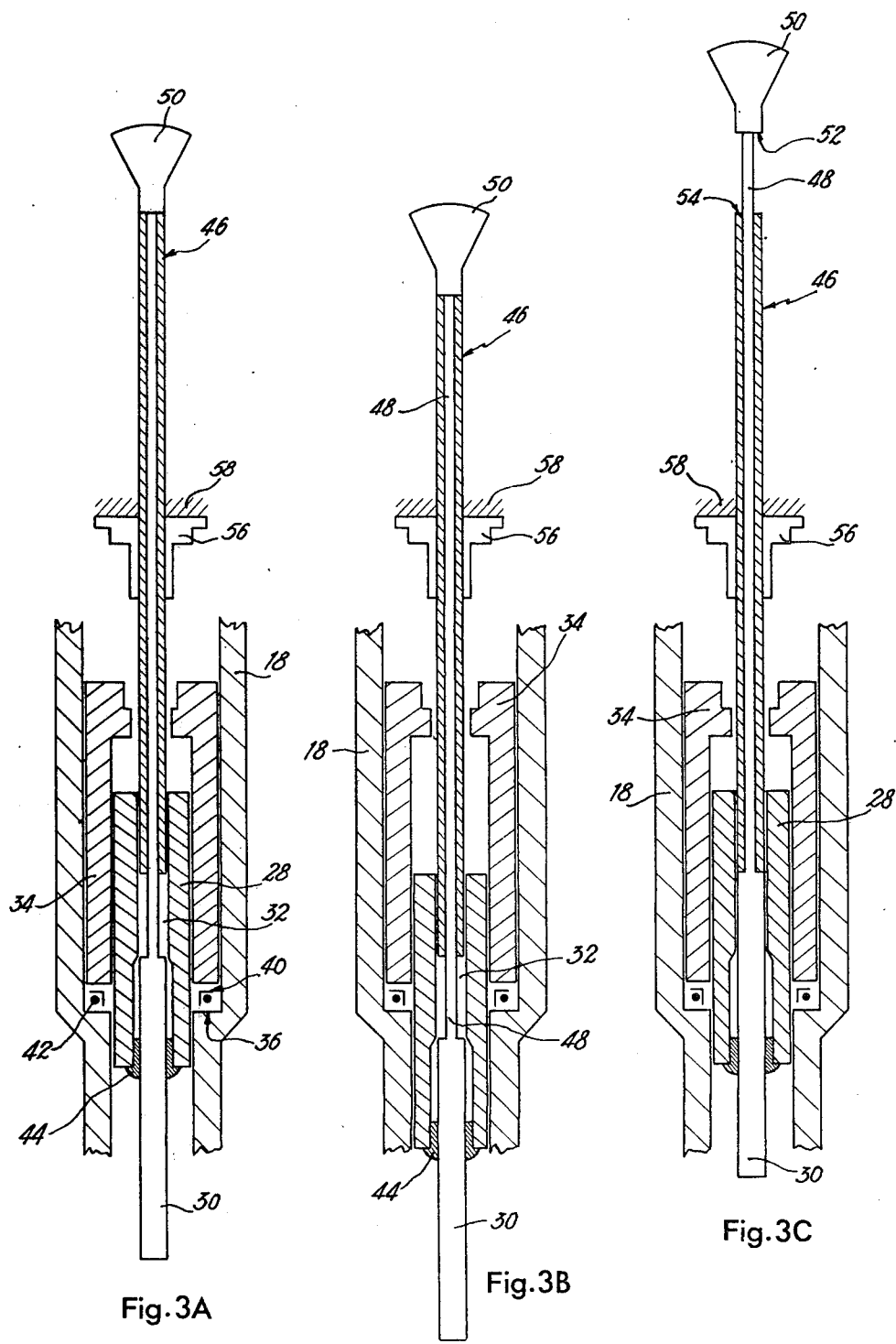

PLURAL PISTON, ADJUSTABLE DILUTING DEVICE HAVING A VOLUME INDICATOR ASSEMBLY

The present invention relates to an adjustable diluting device for mixing a determined volume of a liquid sample and a determined volume of a liquid diluent, at least one of these two volumes being variable.

The diluting device according to the invention makes it possible to draw from a same recipient, rapidly and very precisely, a certain volume of a liquid sample and a certain volume of a liquid diluent, said device being adapted, once the mixture is at the right dilution, to transfer it very rapidly into another container. Due to the diluting device according to the invention, the operator may, by a rapid adjustment, modify for example the volume of the diluent which he proposes to draw and mix it with a predetermined fixed volume of the sample.

In accordance with the present invention, the adjustable diluting device comprises:
- an oblong casing and a lower tapered tubular element or nose member, which are made fast with each other in tight manner;
- a mechanism for adjusting one of the two volumes of sample or diluent drawn up;
- a unit for indicating the adjustable volume of sample or diluent drawn up, said indicator unit being coupled with the adjustment mechanism, and
- a plunger unit adapted for reciprocation in tight manner inside said casing.

In accordance with the present invention, said plunger unit comprises:
- a first piston having a central cylindrical recess opening on its lower surface, said first piston being so arranged as to be able to slide in tight manner in said nose member,
- a second cylindrical piston of circular cross-section adapted to slide in said central cylindrical recess made in the first piston, with the interposition of a frictionally mounted joint between said central cylindrical recess and the first piston,
- a sleeve for controlling the first piston which is fast with said first piston and which presents on its outer surface an annular shoulder, said shoulder being so arranged as to cooperate with a stop limiting the upward stroke of the first piston, which is elastically urged upwardly and which is adjustable in vertical position with respect to the casing by means of said adjustment mechanism,
- a shaft for controlling the second piston, which is fast with said second piston and which may slide inside the sleeve controlling the first piston, and
- a push button fixed to the upper end of the shaft controlling the second piston, the lower part of which button has a stop surface adapted to cooperate with the upper end of the sleeve controlling the first piston.

According to another feature of the present invention, the free end of the nose member of the adjustable diluting device is provided with a removable tip member frictionally mounted on the outer surface of said end. An arrangement of this type avoids any contamination of the actual diluting device, since the liquids drawn come into contact only with the removable conical tip member.

According to another feature of the present invention, the diluting device is equipped with a device for ejecting the removable tip member, which may be actuated by means of a button located near the other control button intended for drawing the sample and the diluent as well as for discharging the mixture thus prepared.

The invention will be more readily understood on reading the following description with reference to the accompanying drawings, in which:

FIGS. 3A, 3B and 3C show the relative positions of the two pistons and their control members at different stages of the constitution of the mixture.

Figure 1:
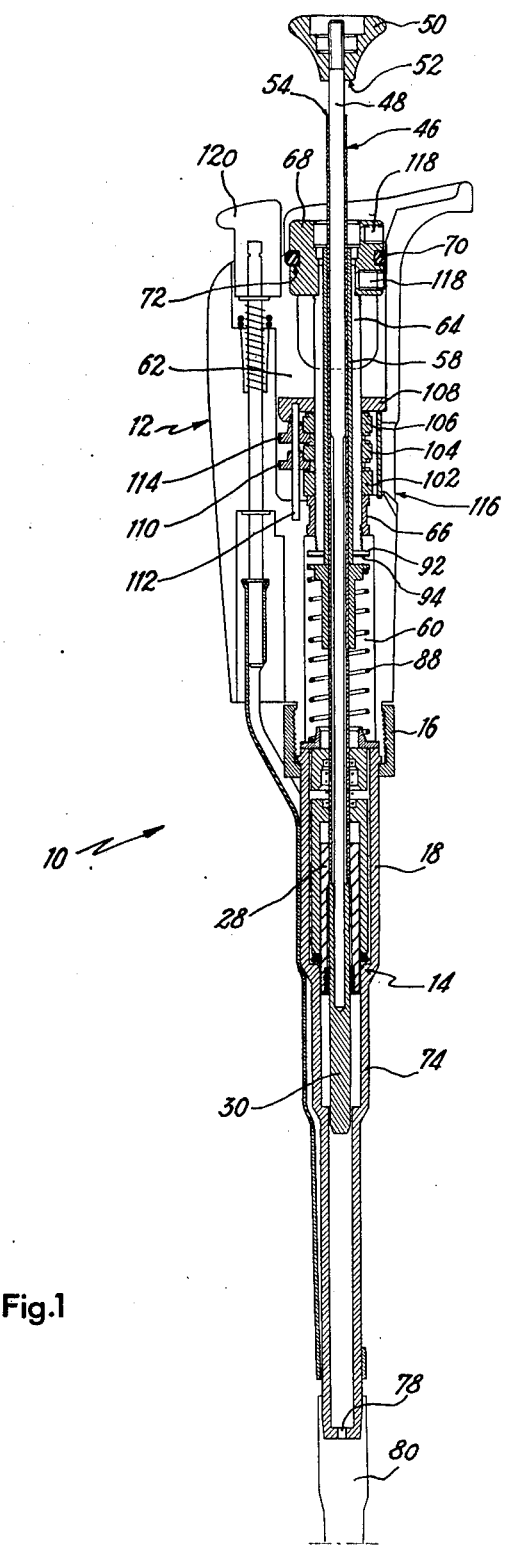
FIG. 1 shows a view in section of the adjustable diluting device according to the invention.

Referring now to the drawings, FIG. 1 shows an adjustable diluting device 10 made in accordance with the invention, which comprises an oblong casing 12 and a lower tapered tubular element or nose member 14. The casing 12 and member 14 are connected tightly together. To obtain this seal, the lower nose member 14 is assembled on the casing 12 by means of a nut 16 screwed on the lower end of the casing 12. The nose member 14 comprises an enlarged upper part 18 internally defining a chamber. An annular assembly rib 20 is firmly held against the lower end of the casing 12 by a face 22 of the nut 16, and a centering washer 24 is imprisoned between the rear end of the nose member 14 and a shoulder 26 defined by a counter-bore at the front end of the cylindrical part of the casing 12.

A plunger unit is adapted to move inside the casing 12 and inside the nose member 14. This plunger unit comprises a first piston 28 and a second cylindrical piston 30 of circular cross-section. The first piston 28 presents a central cylindrical recess 32 opening on its lower surface. This first piston 28 is arranged so as to be able to slide in tight manner inside the nose member 14. This seal may for example be obtained by the interposition, between the outer surface of the first piston 28 and the inner surface of the enlarged upper part 18 of the nose member 14, of a seal seat 34 which, as will appear from the accompanying Figures, is elastically urged downwardly in the direction of the annular shoulder 36. Between the lower surface of the seal seat 34 and the annular shoulder are respectively interposed a Teflon seal 40 and an O-ring 42.

The second cylindrical piston 30 of circular cross-section is adapted to slide in the central cylindrical recess 32 made in the first piston 28. Between the outer surface of the second piston 30 and the inner surface of the first piston 28, near the lower end of said latter, there is interposed a frictionally mounted joint. This joint may advantageously be in the form of a Teglon O-ring 44 made fast, by any known means, with the first piston 28. This frictionally mounted joint acts in fact as a brake and enables the second piston 30 to be immobilised in the position chosen with respect to the first piston 28.

The first piston 28 has been securely connected to a control sleeve 46. To this end, the first piston 28 is press-fitted for example on the control sleeve 46.

A shaft 48 for controlling the second piston 30 is adapted to slide inside the sleeve 46 for controlling the first piston 28. This control shaft 48 is rigidly fixed at the upper end of the second piston 30. At the upper end of said shaft 48 is located a push button 50 which presents at its lower part a stop surface 52 adapted to cooperate with the upper end 54 of the sleeve 46 for controlling the first piston 28.

The Figures show that the rigid assembly constituted by the first piston 28 and by its control sleeve 46 is permanently urged elastically upwardly. To this end, the control sleeve 46 presents on its outer surface a shoulder adapted to cooperate with a stop limiting the upward stroke of the first piston 28, which stop is elastically urged upwardly and is moreover adjustable in vertical position with respect to the casing by means of an adjustment mechanism described hereinafter in greater detail. In the embodiment shown, said shoulder arranged on the outer surface of the control sleeve 46 is made in the form of an inner cylindrical stop 56 press-fitted on the sleeve 46 or fixed by any other means so that it is integral with the sleeve 46. This member 56 is therefore permanently urged upwardly so as to come into intimate contact with the lower end of the stop limiting the stroke of the first piston. This stop which is variable in vertical position is shown in the accompanying drawings by the lower end of a sheath 58 which is made fast with the hollow threaded shaft 64. This sheath 58 must be able to slide on the control sleeve 46 and is placed inside the hollow threaded shaft 64. The aim of the sheath 58, described more completely hereinafter, is to allow the volume-indicator assembly to be adjusted. The lower part of the sheath 58 slightly passes beyond the lower end of the hollow threaded shaft 64, and forms the most advanced part of the volume adjustment assembly. In this way, this lower surface of the sheath 58 comes into permanent contact with the upper surface of the inner stop 56 and therefore serves as stop limiting the upward stroke of the first piston 28.

The casing 12 of the adjustable diluting device according to the invention internally defines a lower cylindrical chamber 60 as well as an upper enlarged cavity 62 adjacent the chamber 60. The upper enlarged cavity 62 incorporates a volume indicating assembly coupled with a volume-adjustment mechanism.

In accordance with the present invention, the adjustment mechanism is intended to vary either one of the two volumes of liquid drawn up, namely either the diluent or the sample. The assembly indicating one of the two volumes of sample or diluent drawn up, which is coupled with said adjustment mechanism, thus makes it possible to make a digital display of the volume thus adjusted.

The adjustment mechanism acting on the vertical position of the sheath 58 with respect to the casing 12 comprises a hollow externally threaded shaft 64 which cooperates with an internally threaded insert 66. This insert 66 is fixed so as to be immobile in rotation and in translation inside the casing 12, for example at the level of the junction between the lower cylindrical chamber 60 and the enlarged upper cavity 62. This hollow threaded shaft 64 must be able to be made fast with the sheath 58 whose lower end constitutes the stop limiting the upward stroke of the first piston 28. On the hollow threaded shaft 64 is externally mounted a nut 68 adapted to drive the hollow threaded shaft 64 in rotation. Consequently, the casing 12 of the diluting device 10 according to the invention must comprise adequate openings allowing said nut 68 to be actuated from outside the casing.

The adjustment mechanism according to the invention also comprises means for restricting the movement of the hollow threaded shaft 64, adapted to immobilise said latter in the position chosen by the operator. In the embodiment described, these means for restricting the movement of the hollow threaded shaft 64 are constituted by a braking ring 70 compressed between the inner surface of the casing 12 and a groove 72 made on the outer surface of the nut 68. This braking ring 70 is advantageously made of flexible, elastically deformable material, resisting wear and tear. To this end, a braking ring will for example be used, made of a material chosen from fluorocarbon resins, polychloroprene and preferably polyurethanes.

Below the part 18 of the nose member 14 is located a part 74 of slightly smaller diameter, internally defining a cylindrical chamber 76 inside which the first piston 28 moves tightly. To avoid the contamination of the sample or diluent liquids drawn up, by the residues of liquid previously drawn up, a removable conical tip member is provided to be frictionally mounted on the outer surface of the free end of the nose member 14. An opening 78 made at the lower end of the nose member 14 communicates the inside of the removable tip member 80 with the interior cavity of the tapered tubular element 14, and in particular with the chamber 76 inside which the first piston 28 moves tightly. The internal volume of the removable tip member 80 is chosen to be sufficiently large to contain all the mixture drawn up, without there being any contact with the lower end of the nose member 14. This tip 80 is preferably made of a non-wetting plastic material to facilitate complete discharge of the samples.

The size and configuration of the adjustable diluting device 10 according to the invention are advantageously chosen to facilitate its use. In particular, the slender configuration of the nose member 14 is intended to permit its insertion into narrow-necked receptacles. The actual casing must be of such configuration as to allow easy grasp by the operator.

Furthermore, the upper part 18 of the nose member 14 internally defines an elastic stop chamber 82, inside which an elastic stop 84 may move against an upwardly directed elastic return force exerted by a spring 86.

In the embodiment described, the plunger unit is elastically urged upwardly by means of a return spring 88 mounted between the shoulder 90 of the inner stop 56 and the upper part of the centering washer 24.

To avoid the whole plunger unit escaping from the casing through the top, for example further to an untimely manoeuvre of the nut 68, the lower end of the hollow threaded shaft 64 terminates in a stop 92 projecting radially towards the outside. This stop 92 may for example be made in the form of a nut screwed at the end of the shaft 64 and immobilised in this position by deformation. A Teflon seal 94 is advantageously placed on the lower surface of the stop 92.

The functioning of the diluting device according to the invention will be explained hereinafter in the case of a mixture being desired of a volume of liquid sample (e.g. 50 $\mu$l) successively with for example 100, 250, 500 and 1000 $\mu$l of liquid diluent.

In such a case, a diluting device should be chosen of which the stroke of the second piston 30 in the cavity 32 of the first piston 28 corresponds to a drawing up of 50 $\mu$l in the tip member 80.

To make the first dilution, the nut 68 of the externally threaded shaft 64 is actuated until the value of 100 $\mu$l is read on the volume indicator rings. The stop surface 52 of the push button 50 is then brought in contact with the upper end of the control sleeve 54, this operation being carried out due to a slight pressure exerted on said button 50 against the force of resistance exerted by the frictionally mounted joint 44 disposed between the two pistons 28 and 30. The plunger unit then occupies the position illustrated in FIG. 3A.

A greater pressure is then exerted on the push button 50, so as to displace the two pistons 28 and 30 and the two control members 46 and 48 downwardly. This downward movement is allowed further to the compression of the return spring 88. The inner stop 56 presents a front end 96 of smaller diameter, provided with a front stop surface 98. The downward movement thus produced provokes the displacement of the stop part 98 due to a central opening 100 made in the centering washer 24 of spring 88, until it comes into contact with the elastic stop 84 mounted in the elastic stop chamber 82 against the lower surface of said centering washer 24. This position is illustrated in FIG. 3B.

The tip member is then immersed in the liquid diluent, and the push button 50 is released. The plunger unit then returns, under the action of the return force exerted by spring 88, into the preceding position illustrated in FIG. 3A. The first piston 28 therefore rises in the inner cavity of part 18 and creates therein a vacuum transmitted inside the removable tip member 80. This vacuum thus enables the 100 μl of diluent to be drawn in the said tip member 80.

The outer surface of the removable tip member 80 is then wiped with a filter paper for example, then it is introduced into the liquid sample.

An upward force is then exerted on the push button 50 so as to lift the shaft 48 into the sleeve 46, this being translated by a rise of the second piston 30 inside the cavity 32 made in the first piston. In this way, a second vacuum is created which is communicated inside the removable tip member 80 and is translated by the drawing up of 50 μl of sample.

Figure 2:
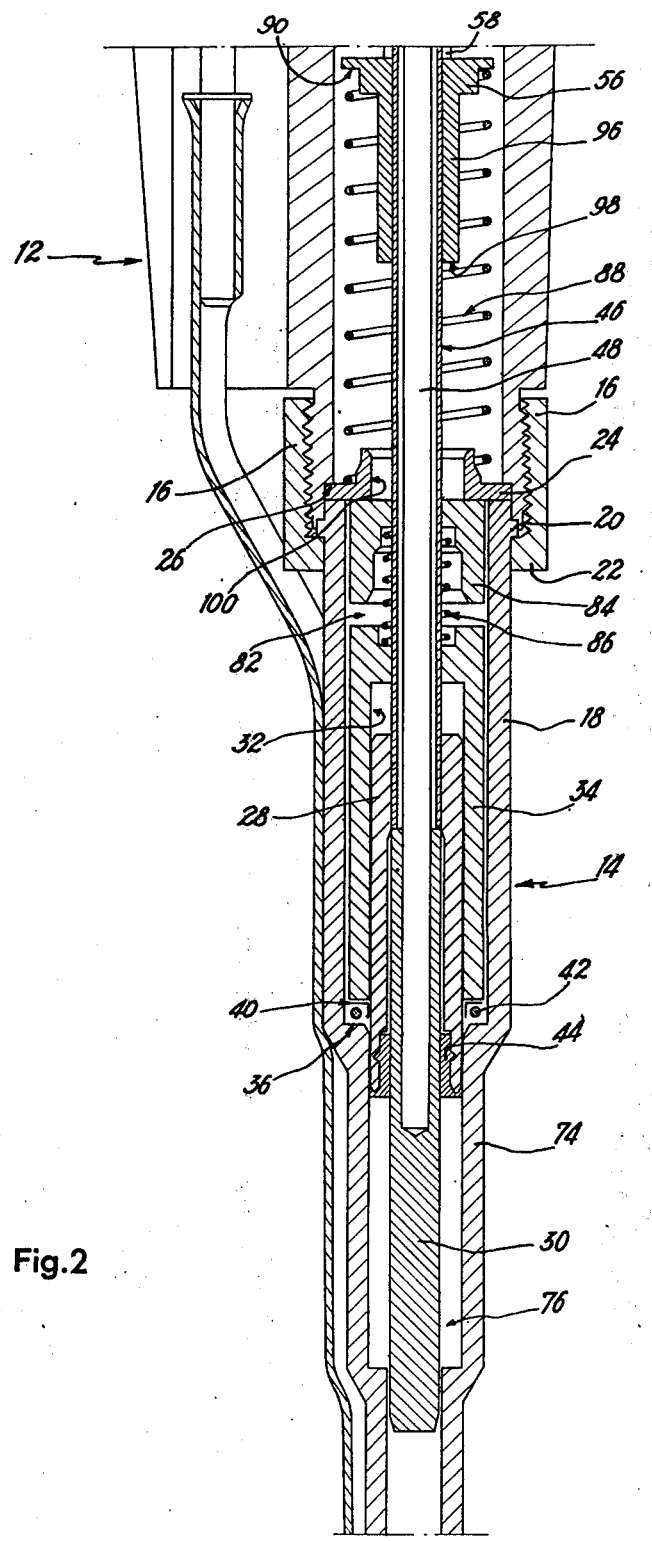
FIG. 2 is a view on a larger scale of that part of the diluting device which comprises the pistons for taking the sample and the diluent.

The desired dilution is thus effected and all that remains is to exert a downward pressure on the push button 50 to discharge this mixture in a container. Upon this delivery stroke, one begins by displacing the second piston 30 then the whole plunger unit downwardly, until the lower stop surface 98 comes into contact with the elastic stop 84. Said latter is maintained at rest in the position illustrated in FIG. 2, by means of the elastic stop spring 86, itself retained compressed between the elastic stop 84 and the seal seat 34; any upward displacement of the elastic stop 84 is prevented by the presence of the shoulder 26 arranged in the lower part of the casing 12.

During the discharge stroke, the plunger unit moves until the stop surface 98 of the part 56 pushes the elastic stop 84 against the elastic stop spring 86 of chamber 82. The result of the movement of this elastic stop 84 is to displace the pistons 28 and 30 in the cavity of the part 18 by a larger stroke than that which corresponded to the suction stroke. It is therefore sure that all the drawn up mixture is completely discharged from the removable tip member 80.

It will be readily understood that it is therefore indispensable to give a positive stop which is easily noticed by the operator at the end of the movement of suction of the diluent. This is why the return spring 88 has less resistance than the elastic stop spring 86. Furthermore, it will be noted that the elastic stop spring fulfills another function, namely it compresses the O-ring 42 and therefore contributes to giving a better tightness near the shoulder 36.

To make the other dilutions, it suffices to replace the removable tip member 80 by a clean one, to adjust the diluting device to 250, 500 and 1000 μl by actuating the adjusting rings and repeat the various operations indicated hereinabove.

An important advantage of the diluting device 10 according to the invention lies in the fact that the operator may very easily adjust one of the volumes of diluent or sample by actuating the nut 68 which causes the hollow externally threaded shaft 64 to rotate and move in translation. The adjustment of the volume to be drawn up is therefore effected by rotating the nut 68 which provokes a translation of the shaft 64 and the sheath 58. This translation therefore provokes the displacement of the stop limiting the upward stroke of the first piston 28, thus adjusting the stroke of the first piston 28 and the volume of liquid drawn up in the first place.

According to another characteristic of the invention, the volume indicator assembly, housed in the casing 12 of the diluting device 10, exactly and legibly translates the position of the volume adjustment mechanism. A series of volume indicator rings 102, 104 and 106, each fitted on the hollow externally threaded shaft 64, is stacked inside the enlarged upper cavity 62, between the insert 66 and the snap-on cap 108. In the embodiment illustrated in the accompanying drawings, the rings 102, 104 and 106 indicate respectively the volume adjustments in units, tens and hundreds of microliters ($mm^3$). However, it is clear that it is possible to provide more or fewer rings graduated in any desired unit.

To couple the volume indicator assembly with the volume adjustment assembly, the hollow threaded shaft 64 comprises, from one end to the other, a longitudinal groove (not shown in the accompanying Figures). The units ring 102 comprises an inwardly projecting protuberance (not shown) which is inserted in said groove in order to rotate the ring 102 with the threaded shaft 64, whilst allowing the axial displacement of said shaft 64 with respect to the rings. The tens ring 104 and the hundreds ring 106 are free to rotate independently of the shaft 64.

The movement of the rings 102, 104 and 106 with respect to one another is effected in conventional manner. For a full revolution of the units ring 102, a single pair of teeth drives a spur gear 110 mounted on a shaft 112 which passes through the enlarged upper cavity 62 of the casing 12. The spur gear 110 engages continuous gears on the tens ring 104 to move it by a tenth of a revolution. Similarly, a full revolution of the tens ring 104 results in incremental movement of the hundreds ring 106 by virtue of a single pair of gear teeth, an additional spur gear 114 and a continuous gear on the hundreds ring 106. As shown in FIG. 1, a transparent window 116 has been provided in the wall of the casing 12 for viewing the indicator rings 102, 104 and 106.

To assure accuracy of the indication given by the volume indicator assembly, an initial zero adjustment is provided during the manufacture. In the initial manufacture and assembly of the diluting device 10, the rings 102, 104 and 106 are mounted so that a zero indication appears when the hollow threaded shaft 64 is screwed inwardly approximately until the stop surface of the inner stop 56 comes into contact with the elastic stop 84 in its high position. It is precisely to adjust the position of the zero that the function of the sheath 58 comes into play. The nut 68 is rotated until the volume indicator assembly exactly indicates the zero. At that moment, the screw retainers 118 are loosened and the nut 68 may be rotated while the shaft 64 remains stationary. During this rotation, the reading of the volume indicator is not changed. However, the rotation of the nut 68 advances or retracts the sheath 58 with respect to the shaft 64, precisely to locate the plunger unit at the zero volume position. When this position has been reached, the screw retainers 118 are tightened once again and the zero adjustment is thus completed.

In the embodiment described previously, it has been considered that only one of the two volumes of sample or diluent was adjustable. However, the diluter 10 according to the invention always advantageously comprises means enabling the position of the push button 50 to be adjusted with respect to the shaft 48 of the second piston 30. These means may for example be produced by a simple threading in the upper part of the control shaft 48, this latter being intended to cooperate with a threaded blind hole made in the lower part of the push button 50. The fact of screwing the button 50 more or less deeply on the control shaft 48 influences the stroke of the second piston 30 with respect to the first piston 28. This operation will therefore vary the volume drawn up further to the depression created by the displacement of the second piston 30 inside the cavity 32 made in the first piston 28.

These adjustment means may have for sole function to effect an adjustment for correcting, in very small proportions, the drawn up volume. On the other hand, it is possible to mount the push button 50 on the shaft 48 by interposing a vernier device. In this case, it will also be possible to vary the second volume drawn up and a digital display of this second volume will also be available.

According to a further characteristic of the present invention, the diluting device 10 is also equipped with a device allowing the automatic ejection of the removable tip members 80. This device, illustrated in particular in FIG. 1 will not be described in greater detail, having already formed the subject matter of French Pat. No. 74 34588 filed by Applicant. The device for automatically ejecting removable tip members is actuated by means of a button 120 located near push button 50. This close arrangement of the two control buttons 50 and 120 enables the operator to carry out all the operations of drawing up, discharge and ejection of the removable tip member 80 with one hand.

What is claimed is:

1. In an adjustable diluting device for mixing a determined volume of a liquid sample and a determined volume of a liquid diluent, at least one of these two volumes being variable, the combination of:

an oblong casing and a lower tapered tubular element or nose member made fast with said casing;

a mechanism for adjusting one of the two volumes of sample or diluent drawn up;

a unit for indicating the adjustable volume of sample or diluent drawn up, said indicator unit being coupled with said adjustment mechanism;

a plunger unit mounted for reciprocation in tight manner inside said casing and said nose member, said plunger unit itself comprising:

two coaxial pistons of which the first piston slides tightly inside the nose member and the second piston slides inside a central recess made in the first piston;

a sleeve for controlling the first piston, and to cooperate with a stop for limiting the upward stroke of the first piston, said stop being elastically urged upwardly and being adjustable in vertical position by means of said adjustment mechanism;

a shaft for controlling the second piston, which may slide inside said sleeve controlling the first piston, and a push button fixed to the upper end of said shaft for controlling the second piston, and having a stop surface cooperating with the upper end of the sleeve to control the first piston;

said casing internally defining a lower cylindrical chamber and an upper enlarged cavity, adjacent said latter, and incorporating said indicator assembly coupled with said adjustment mechanism, said latter comprising:

a hollow shaft externally cooperating by screwing with an insert fixed so as to be immobile in rotation and in translation inside said casing, said hollow threaded shaft comprising, near its lower end, said stop limiting the upward stroke of the first piston;

a nut for rotating said hollow threaded shaft, adapted to be actuated from outside the casing;

volume indicator rings bearing indices visible through a window made in the casing, said rings being fixed on said threaded shaft so as to surround it and allow it an alternative movement through the rings which moreover are equipped with drive means for controlling the relative movement of said rings depending on the movement of rotation of the hollow threaded shaft, and means for restricting the movement of said hollow threaded shaft for immobilizing said shaft in a chosen position.

2. The diluting device as recited in claim 1, further comprising an elastic stop chamber arranged in the upper part of the nose member, an elastic stop mounted to move in said elastic stop chamber against an upwardly directed elastic return force, exerted by an elastic stop spring.

3. The diluting device as recited in claim 2, wherein the stop limiting the upward stroke of the first piston is elastically urged upwardly by means of a return spring having a resistance at least substantially lower than that of said elastic stop spring.

4. The diluting device as recited in claim 1, wherein said means for restricting the movement of the hollow threaded shaft are constituted by a braking ring compressed between the inner surface of the casing and a groove made in the outer surface of the nut for rotating said hollow threaded shaft.

5. The diluting device as recited in claim 4, wherein said braking ring is made of a supple, elastically deformable material, resistant to wear and tear, such as for example a fluorocarbon resin, polychloroprene or preferably polyurethanes.

6. The diluting device as recited in claim 1, wherein the stop limiting the upward stroke of the first piston is adjustable in position with respect to the lower end of the hollow threaded shaft, wherein said stop being coupled to said indicator rings that indicate volume as a function of the precise position of said stop limiting the upward stroke of the first piston.

7. The diluting device as recited in claim 1, further comprising means for adjusting the position of the push button with respect to the shaft controlling the second piston.

8. The diluting device as recited in claim 7, wherein said means for adjusting the position of the push button with respect to said control rod are constituted by a threading, arranged at the upper end of said control rod, for cooperating with a threaded blind hole made in said push button.

9. The diluting device as recited in claim 1, wherein the free end of the nose member is equipped with a removable conical tip member frictionally mounted on the outer surface of said end.

10. The diluting device as recited in claim 9, further equipped with a device for ejecting the removable tip member, actuated by means of a button located near the pushbutton of said shaft controlling the second piston.

* * * * *